United States Patent
Terakawa et al.

(10) Patent No.: US 8,124,669 B2
(45) Date of Patent: Feb. 28, 2012

(54) DENTAL COMPOSITION

(75) Inventors: Eiichi Terakawa, Chiyoda-ku (JP);
Akiko Ota, Kurashiki (JP); Takahiro Sekiguchi, Kurashiki (JP)

(73) Assignee: Kuraray Medical Inc., Kurashiki-shi (JP)

( * ) Notice: Subject to any disclaimer, the term of this patent is extended or adjusted under 35 U.S.C. 154(b) by 313 days.

(21) Appl. No.: 12/526,442

(22) PCT Filed: Feb. 5, 2008

(86) PCT No.: PCT/JP2008/051863
§ 371 (c)(1),
(2), (4) Date: Aug. 7, 2009

(87) PCT Pub. No.: WO2008/096753
PCT Pub. Date: Aug. 14, 2008

(65) Prior Publication Data
US 2011/0003267 A1    Jan. 6, 2011

(30) Foreign Application Priority Data
Feb. 8, 2007    (JP) .................. 2007-029307

(51) Int. Cl.
*A61K 6/083*    (2006.01)
*A61C 5/04*    (2006.01)

(52) U.S. Cl. ...................... 523/116; 433/228.1; 977/919

(58) Field of Classification Search .................. 523/116; 433/228.1
See application file for complete search history.

(56) References Cited

U.S. PATENT DOCUMENTS

| | | | |
|---|---|---|---|
| 6,030,606 A | 2/2000 | Holmes | |
| 6,232,367 B1 * | 5/2001 | Kobashigawa et al. | 523/116 |
| 6,528,555 B1 | 3/2003 | Nikutowski et al. | |
| 6,593,395 B2 * | 7/2003 | Angeletakis et al. | 523/115 |
| 7,906,564 B2 * | 3/2011 | Jia et al. | 523/116 |
| 2002/0013382 A1 | 1/2002 | Furman et al. | |
| 2003/0181541 A1 | 9/2003 | Wu et al. | |
| 2008/0242761 A1 * | 10/2008 | Jia et al. | 523/118 |

FOREIGN PATENT DOCUMENTS

| | | |
|---|---|---|
| JP | 63-303906 | 12/1988 |
| JP | 2002-518419 | 6/2002 |
| JP | 2004-510796 A | 4/2004 |
| JP | 2005-517688 | 6/2005 |
| JP | 2007-8972 | 1/2007 |

* cited by examiner

*Primary Examiner* — Tae H Yoon
(74) *Attorney, Agent, or Firm* — Oblon, Spivak, McClelland, Maier & Neustadt, L.L.P.

(57) ABSTRACT

A composition for dental use containing a polymerizable monomer (a) having an aromatic ring and a hydroxyl group, a polymerizable monomer (b) having an aromatic ring without having any hydroxyl groups, and a polymerizable monomer (c) other than the polymerizable monomers (a) and (b), wherein the composition for dental use contains the polymerizable monomers (a), (b), and (c) in an amount of from 10 to 30% by weight, from 50 to 70% by weight, and from 10 to 30% by weight, respectively, of all the polymerizable monomers. The composition for dental use of the present invention can be suitably used as a product capable of substituting a part or all of a natural tooth in the field of dental therapy.

9 Claims, No Drawings

DENTAL COMPOSITION

TECHNICAL FIELD

The present invention relates to a composition for dental use which is capable of substituting a part or all of a natural tooth in the field of dental therapy.

BACKGROUND ART

A composite resin constituted by a polymerizable monomer, an inorganic filler, and a polymerization initiator is the most well used material today as a material for filling and restoring fracture of teeth and dental caries.

Patent Publication 1 discloses a technique of obtaining an artificial dental material having high transparency, and excellent mechanical strength and polishing property by polymerizing and curing a composition prepared by mixing in a specified blending ratio a fine alumina powder having specified refractive index and particle size, an inorganic filler having specified refractive index and particle size, and having radiopacity, and a polymerizable monomer having a specified refractive index. Patent Publication 1: Japanese Patent Laid-Open No. Sho 63-303906

DISCLOSURE OF THE INVENTION

Problems to be Solved by the Invention

Conventional materials undergo changes in transparency before and after the polymerization of compositions. For example, in a direct filling restoration, a composition is allowed to polymerize after a dentist matches the color of the teeth of patients and fillers, so that when a change in transparency is large, a desired color is not obtained, thereby making it likely to impair their aesthetic appreciation. In addition, a composition may have poor adhesive properties to an adhesive for dental use, depending upon the kinds of the fillers used. On the other hand, when inorganic particles are contained in a large amount in order to maintain the strength, there are some disadvantages that the composition becomes rigid or dry and loose, thereby impairing the operability of the direct filling restoration, so that a desired shape cannot be obtained.

An object of the present invention is to provide a composition for dental use having excellent mechanical strength and operability, and further having a small change in transparency before and after the polymerization, and having excellent adhesive properties.

Means to Solve the Problems

As a result of intensive studies in order to solve the above problems, the present inventors have found that a composition for dental use having excellent mechanical strength and operability, and further having a small change in transparency before and after the polymerization, and having excellent adhesive properties is obtained by blending specified polymerizable monomers in a specified ratio. The present invention has been perfected thereby.

Specifically, the present invention relates to a composition for dental use containing a polymerizable monomer (a) having an aromatic ring and a hydroxyl group, a polymerizable monomer (b) having an aromatic ring without having any hydroxyl groups, and a polymerizable monomer (c) other than the polymerizable monomers (a) and (b), wherein the composition for dental use contains the polymerizable monomers (a), (b), and (c) in an amount of from 10 to 30% by weight, from 50 to 70% by weight, and from 10 to 30% by weight, respectively, of all the polymerizable monomers.

Effects of the Invention

The composition for dental use of the present invention exhibits excellent effects that the composition has excellent mechanical strength and operability, and further has a small change in transparency before and after the polymerization, and excellent adhesive properties.

BEST MODE FOR CARRYING OUT THE INVENTION

One of the features of the composition for dental use of the present invention is in that the composition contains a polymerizable monomer (a) having an aromatic ring and a hydroxyl group, a polymerizable monomer (b) having an aromatic ring without having any hydroxyl groups, and a polymerizable monomer (c) other than the polymerizable monomers (a) and (b), wherein the composition for dental use contains the polymerizable monomers (a), (b), and (c) in amounts of specified ranges of all the polymerizable monomers.

The polymerizable monomer (a) having an aromatic ring and a hydroxyl group is not particularly limited, so long as the polymerizable monomer is a polymerizable monomer having an aromatic ring and having a hydroxyl group, and the polymerizable monomer has at least one hydroxyl group, at least one aromatic ring, and at least one polymerizable group, and the number of the hydroxyl groups, the aromatic rings, and the polymerizable groups are not particularly limited. The number of the polymerizable groups is preferably from 1 to 6, and more preferably from 2 to 4, from the viewpoint of easy availability and mechanical strength of a cured product of the composition for dental use. The number of the hydroxyl groups is preferably from 1 to 3, from the viewpoint of easy availability and hydrophilicity of the composition for dental use. The number of the aromatic rings is preferably from 1 to 3, and more preferably 2, from the viewpoint of easy availability and mechanical strength of a cured product of the composition for dental use. It is especially preferable that the polymerizable monomer (a) has a bisphenol A backbone, i.e. a structure of bisphenol A without hydrogen atoms on two hydroxyl groups. Examples of the polymerizable monomer (a) as mentioned above include 2,2-bis[4-[3-(meth)acryloyloxy-2-hydroxypropoxy]phenyl]propane (which may be hereinafter referred to as Bis-GMA), 2-[4-[3-(meth)acryloyloxy-2-hydroxypropoxy]phenyl]-2-[4-[2,3-di(meth)acryloyloxypropoxy]phenyl]propane (which may be hereinafter referred to as Bis3), 2-[4-[3-(meth)acryloyloxy-2-hydroxypropoxy]phenyl]-2-[4-(meth)acryloyloxydiethoxyphenyl]propane, 2-[4-[3-(meth)acryloyloxy-2-hydroxypropoxy]phenyl]-2-[4-(meth)acryloyloxytriethoxyphenyl]propane, 2-[4-[3-(meth)acryloyloxy-2-hydroxypropoxy]phenyl]-2-[4-(meth)acryloyloxydipropoxyphenyl]-propane, and the like. These polymerizable monomers can be used alone or in a proper combination of two or more kinds. Among these polymerizable monomers, Bis-GMA is preferred, from the viewpoint of increasing mechanical strength of a cured product of the composition for dental use and bond strength with the teeth.

The polymerizable monomer (b) having an aromatic ring without having any hydroxyl groups is not particularly limited, so long as the polymerizable monomer is a polymerizable monomer having an aromatic ring without having any hydroxyl groups, and the polymerizable monomer has at least one aromatic ring and at least one polymerizable group without having any hydroxyl groups, and the number of the aromatic rings and the polymerizable groups is not particularly limited. The number of the polymerizable groups is preferably from 1 to 6, and more preferably from 2 to 4, from the viewpoint of easy availability and mechanical strength of a cured product of the composition for dental use. The number of the aromatic rings is preferably from 1 to 3, and more preferably 2, from the viewpoint of easy availability and mechanical strength of a cured product of the composition for dental use. It is especially preferable that the polymerizable monomer (b) has a bisphenol A backbone. Examples of the polymerizable monomer (b) as mentioned above include a compound represented by the formula (I):

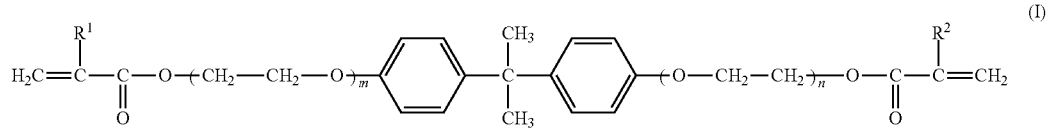

wherein each of $R^1$ and $R^2$ is a hydrogen atom or a methyl group, and m and n are 0 or positive numbers showing an average number of moles of an ethoxy group added, wherein the sum of m and n is preferably from 1 to 6, and more preferably from 2 to 4,
including, for example, 2,2-bis[4-(meth)acryloyloxypolyethoxyphenyl]-propane in which m and n satisfy the formula of m+n=2.6 (which may be hereinafter referred to as D2.6E); 2,2-bis[4-(meth)acryloyloxypolyethoxyphenyl]propane, which is 2,2-bis[4-(meth)acryloyloxytriethoxyphenyl]propane in which m and n satisfy the formula of m+n=6 (which may be hereinafter referred to as D6E); 2,2-bis[4-(meth)acryloyloxyphenyl]propane (m and n satisfy the formula of m+n=0); 2-[4-(meth)acryloyloxyethoxyphenyl]-2-[4-(meth) acryloyloxyphenyl]propane (m and n satisfy the formula of m+n=1); 2,2-bis[4-(meth)acryloyloxyethoxyphenyl]propane (m and n satisfy the formula of m+n=2); 2-[4-(meth)acryloyloxydiethoxyphenyl]-2-[4-(meth)acryloyloxyethoxyphenyl] propane (m and n satisfy the formula of m+n=3); 2,2-bis[4-(meth)acryloyloxydiethoxyphenyl]propane (m and n satisfy the formula of m+n=4); 2-[4-(meth)acryloyloxydiethoxyphenyl]-2-[4-(meth)acryloyloxytriethoxyphenyl]propane (m and n satisfy the formula of m+n=5), and the like. In addition, as the polymerizable monomer (b), 2,2-bis[4-(meth)acryloyloxydipropoxyphenyl]propane, 2-[4-(meth) acryloyloxydipropoxyphenyl]-2-[4-(meth)acryloyloxytriethoxyphenyl]propane, 2,2-bis[4-(meth) acryloyloxypropoxyphenyl]propane, 2,2-bis[4-(meth) acryloyloxyisopropoxyphenyl]propane, or the like can be used. These polymerizable monomers can be used alone or in an appropriate combination of two or more kinds. Among them, D2.6E and D6E are preferred, from the viewpoint of properties (precipitation property or the like) of the polymerizable monomer.

The polymerizable monomer (c) is not particularly limited so long as the polymerizable monomer is a polymerizable monomer other than (a) and (b). The polymerizable monomer (c) includes a polymerizable monomer (c-1) without having any aromatic rings and without having any hydroxyl groups, and a polymerizable monomer (c-2) without having any aromatic rings and having a hydroxyl group. The number of the polymerizable groups is preferably from 1 to 6, from the viewpoint of easy availability and mechanical strength of a cured product of the composition for dental use.

The polymerizable monomer (c-1) without having any aromatic rings and without having any hydroxyl groups includes, for example, methyl(meth)acrylate, ethyl(meth)acrylate, propyl(meth)acrylate, isopropyl(meth)acrylate, butyl(meth) acrylate, isobutyl(meth)acrylate, lauryl(meth)acrylate, 2,3-dibromopropyl(meth)acrylate, (meth)acrylamide, ethylene glycol di(meth)acrylate, triethylene glycol di(meth)acrylate (which may be hereinafter referred to as 3G), 1,2-butanediol di(meth)acrylate, neopentyl glycol di(meth)acrylate, propylene glycol di(meth)acrylate, 1,3-butanediol di(meth)acrylate, 1,4-butanediol di(meth)acrylate, 1,6-hexanediol di(meth)acrylate, 1,10-decanediol di(meth)acrylate (which may be hereinafter referred to as DD), N,N'-(2,2,4-trimethylhexamethylene)bis[2-(aminocarboxy)ethan-1-ol]di(meth) acrylate (which may be hereinafter referred to as UDMA), N,N'-(2,2,4-trimethylhexamethylene)bis[2-(aminocarboxy) propane-1,3-diol]tetra(meth)acrylate, trimethylolpropane tri (meth)acrylate, trimethylolethane tri(meth)acrylate, pentaerythritol tetra(meth)acrylate, N,N'-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxyheptane.

The polymerizable monomer (c-2) without having any aromatic rings and having a hydroxyl group includes, for example, 2-hydroxyethyl (meth)acrylate, 2-hydroxypropyl (meth)acrylate, 3-hydroxypropyl (meth)acrylate, 1,3-dihydroxypropyl(meth)acrylate, 2,3-dihydroxypropyl (meth) acrylate, 2-hydroxyethyl(meth)acrylamide, 1,2-bis(3-methacryloyloxy-2-hydroxypropoxy)ethane, diethylene glycol (meth)acrylate, pentaerythritol di(meth)acrylate, and tetramethylolmethane tri(meth)acrylate. These polymerizable monomers can be used alone or in a proper combination of two or more kinds. Incidentally, the term "(meth)acrylate" as used herein refers to a generic name for acrylic acid ester and a methacrylic acid ester.

It is preferable that the polymerizable monomer (a) has a hydrophilic group (hydroxyl group) having a high affinity to the teeth, and that the polymerizable monomer is contained in a higher amount, from the viewpoint of adhesive properties to the teeth. However, since the polymerizable monomer (a) has a high viscosity, in a case where the polymerizable monomer is contained in a large amount, the composition becomes sticky, thereby being disadvantageous in operability. The polymerizable monomer (a) is contained in an amount of from 10 to 30% by weight, and preferably from 15 to 25% by weight, of the all the polymerizable monomers, from the viewpoint of adhesive properties to the teeth.

The polymerizable monomer (b) has a refractive index of nearly the same level as the polymerizable monomer (a), but has a property of low viscosity, as compared to that of the polymerizable monomer (a). The polymerizable monomer (b) can improve the operability of the composition, while maintaining the refractive index of the all the polymerizable monomers at the refractive index of the polymerizable monomer (a). However, if the polymerizable monomer (b) is contained in a larger amount, the composition has a lowered viscosity, so that the formability is impaired. The polymerizable monomer (b) is contained in an amount of from 50 to 70% by weight, and preferably from 55 to 70% by weight, of the all the polymerizable monomers, from the viewpoint of transparency and operability.

The ratio of a weight of the polymerizable monomer (a) to a weight of the polymerizable monomer (b), i.e. polymerizable monomer (a)/polymerizable monomer (b), is preferably from 0.15 to 0.6, and more preferably from 0.25 to 0.45, from the viewpoint of operability of the composition.

The polymerizable monomer (c) has the properties of a low refractive index and a low viscosity, as compared to those of the polymerizable monomer (a) and the polymerizable monomer (b). If the polymerizable monomer (c) is contained in a too small amount, the viscosity of the composition becomes high, so that operability is impaired. On the other hand, if the polymerizable monomer (c) is contained in a too large amount, the refractive index of the all the polymerizable monomers is lowered, so that the balance in the refractive indices of the overall composition is lost, thereby impairing a change in transparency before and after the polymerization. The polymerizable monomer (c) is contained in an amount of from 10 to 30% by weight, and preferably from 15 to 25% by weight, of all the polymerizable monomers, from the viewpoint of operability. Here, all the polymerizable monomers of the present invention are constituted by the polymerizable monomers (a), (b) and (c).

Since the polymerizable monomer (a), the polymerizable monomer (b) and the polymerizable monomer (c) are contained in amounts so that the polymerizable monomers are blended in a good balance in a specified ratio with setting the amount of the polymerizable monomer (b) to be larger as mentioned above, a desired composition for dental use having excellent adhesive properties and operability, having high transparency of a cured product, and having a small change in transparency before and after the polymerization can be obtained. The ratio of a weight of the polymerizable monomer (a) to a weight of the polymerizable monomer (c), i.e. polymerizable monomer (a)/polymerizable monomer (c), is preferably from 0.35 to 3, more preferably from 0.5 to 2, and most preferably from 0.7 to 1.3, from the viewpoint of satisfying operability of the composition and reduction of a change in transparency before and after the polymerization in an even higher level.

In addition, in the present invention, the polymerizable monomers (a) to (c) are blended, and a mixture can be used as a polymerizable monomer composition. It is preferable that the polymerizable monomers (a) to (c) are blended in an amount so as to have a composition in which a refractive index of a polymerized and cured product of the polymerizable monomer composition is within the range of from 1.5 to 1.7. Especially, the polymerizable monomers are used so as to have a composition in which the lower limit of the refractive index of the polymerized and cured product is more preferably 1.52 or more, and even more preferably 1.53 or more. In a case where an especially high transparency is necessitated, it is preferable that the composition is designed so that the refractive index of the polymerized and cured product is approximated to the refractive index of alumina particles (d) described later. Here, the refractive index of the polymerized and cured product of the polymerizable monomer composition as used herein is measured in accordance with the method described in Examples set forth below.

The polymerizable monomer can be polymerized in accordance with a known method, and a polymerization initiator, such as a photopolymerization initiator, a thermal polymerization initiator, or a chemical polymerization initiator can be used, if needed.

The photopolymerization initiator includes, for example, an α-diketone/reducing agent, a ketal/reducing agent, a thioxanthone/reducing agent, and the like. Examples of the α-diketone include camphorquinone, benzyl, 2,3-pentanedione, and the like. Examples of the ketal include benzyl dimethyl ketal, benzyl diethyl ketal, and the like. Examples of the thioxanthone include 2-chlorothioxanthone, 2,4-diethylthioxanthone, and the like. Examples of the reducing agent include tertiary amines such as 2-(dimethylamino)ethyl methacrylate, N,N-bis[(meth)acryloyloxyethyl]-N-methylamine, ethyl 4-dimethylaminobenzoate, butyl 4-dimethylaminobenzoate, butoxyethyl 4-dimethylaminobenzoate, N-methyldiethanolamine, 4-dimethylaminobenzophenone, N,N-di(2-hydroxyethyl)-p-toluidine, and dimethylaminophenanthrol; aldehydes such as dimethylaminobenzaldehyde and terephthalaldehyde; compounds having a thiol group, such as 2-mercaptobenzooxazole, decanethiol, 3-mercaptopropyl trimethoxysilane, and thiobenzoic acid; and the like. In addition, when a photopolymerization by irradiation with ultraviolet rays is carried out, an alkyl ether of benzoin, benzyl dimethyl ketal, or the like is preferred. Further, a (bis)acyl phosphine oxide photopolymerization initiator is preferably used. Among the (bis)acyl phosphine oxides, the acyl phosphine oxide includes, for example, 2,4,6-trimethylbenzoyl diphenyl phosphine oxide, 2,6-dimethoxybenzoyl diphenyl phosphine oxide, 2,6-dichlorobenzoyl diphenyl phosphine oxide, 2,4,6-trimethylbenzoyl methoxyphenyl phosphine oxide, 2,4,6-trimethylbenzoyl ethoxyphenyl phosphine oxide, 2,3,5,6-tetramethylbenzoyl diphenyl phosphine oxide, benzoyl di-(2,6-dimethylphenyl) phosphonate, and the like. The bis-acyl phosphine oxide includes, for example, bis-(2,6-dichlorobenzoyl)phenyl phosphine oxide, bis-(2,6-dichlorobenzoyl)-2,5-dimethylphenyl phosphine oxide, bis-(2,6-dichlorobenzoyl)-4-propylphenyl phosphine oxide, bis-(2,6-dichlorobenzoyl)-1-naphthyl phosphine oxide, bis-(2,6-dimethoxybenzoyl)phenyl phosphine oxide, bis-(2,6-dimethoxybenzoyl)-2,4,4-trimethylpentyl phosphine oxide, bis-(2,6-dimethoxybenzoyl)-2,5-dimethylphenyl phosphine oxide, bis-(2,4,6-trimethylbenzoyl)phenyl phosphine oxide, (2,5,6-trimethylbenzoyl)-2,4,4-trimethylpentyl phosphine oxide, and the like. These (bis)acyl phosphine oxide photopolymerization initiators can be used alone or also together with a reducing agent, such as various amines, aldehydes, mercaptans, or sulfinates. The (bis)acyl phosphine oxide photopolymerization initiator can also favorably used together with the photopolymerization initiator for visible light.

The thermal polymerization initiators include, for example, organic peroxides, such as diacyl peroxides, peroxy esters, dialkyl peroxides, peroxy ketals, ketone peroxides, and hydroperoxides. Specific examples thereof are as follows. The diacyl peroxides include benzoyl peroxide, 2,4-dichlorobenzoyl peroxide, m-toluoyl peroxide, and the like. The peroxy esters include, for example, t-butylperoxy benzoate, bis-t-butylperoxy isophthalate, 2,5-dimethyl-2,5-bis(benzoylperoxy)hexane, t-butylperoxy-2-ethyl hexanoate, and t-butylperoxy isopropyl carbonate. The dialkyl peroxides include, for example, dicumyl peroxide, di-t-butyl peroxide, and lauroyl peroxide. The peroxy ketals include, for example, 1,1-bis(t-butylperoxy) 3,3,5-trimethylcyclohexane. The ketone peroxides include, for example, methyl ethyl ketone peroxide. The hydroperoxides include, for example, t-butyl hydroperoxide, and the like.

As the chemical polymerization initiator, for example, a redox polymerization initiator, such as an organic peroxide/amine mixture or an organic peroxide/amine/sulfinic acid (or a salt thereof) mixture is preferably used. When the redox polymerization initiator is used, it is necessary to have a wrapping form in which an oxidizing agent and a reducing agent are separately wrapped, to mix both the components immediately before use. Alternatively, there is a case where the components are mixed with a static mixer or the like and used. The oxidizing agent includes the same organic peroxides as the thermal polymerization initiator mentioned above. As the reducing agent, a tertiary amine is usually used, and the tertiary amine includes, for example, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-i-propylaniline, N,N-dimethyl-4-t-butylaniline, N,N-dimethyl-3,5-di-t-butylaniline, N,N-di(2-hydroxyethyl)-p-toluidine, N,N-di(2-hydroxyethyl)-3,5-dimethylaniline, N,N-di(2-hydroxyethyl)-3,4-dimethylaniline, N,N-di(2-hydroxyethyl)-4-ethylaniline, N,N-di(2-hydroxyethyl)-4-i-propylaniline, N,N-di(2-hydroxyethyl)-4-t-butylaniline, N,N-di(2-hydroxyethyl)-3,5-di-1-propylaniline, N,N-di(2-hydroxyethyl)-3,5-di-t-butylaniline, ethyl 4-dimethylaminobenzoate, n-butoxyethyl 4-dimethylaminobenzoate, (2-methacryloyloxy)ethyl 4-dimethylaminobenzoate, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The polymerization initiator is added in an amount of preferably from 0.01 to 10 parts by weight, and more preferably from 0.1 to 5 parts by weight, based on 100 parts by weight of all the polymerizable monomers.

It is preferable that the composition for dental use of the present invention further contains specified alumina particles (d), from the viewpoint of increasing mechanical strength.

The alumina particles (d) in the present invention satisfy the two requirements:
(i) a refractive index ($n_A$) is from 1.60 to 1.70, and
(ii) a proportion of particles having particle sizes of from 0.005 to 0.1 μm is 95% by number or more.

The alumina particles exist, in addition to α-form, in crystal transformations of γ-form, δ-form, χ-form, κ-form, ρ-form, η-form, and θ-form. While the α-alumina has a refractive index of from 1.76 to 1.768, these crystal transformations have refractive indices within the range of from 1.60 to 1.70. The alumina particles (d) used in the present invention are not particularly limited in the crystal form, so long as the alumina particles have a refractive index ($n_A$) of from 1.60 to 1.70, and preferably from 1.60 to 1.65, from the viewpoint of reducing the difference with the refractive index of the polymer. Here, in a case where two or more kinds of alumina particles having different crystal forms are used, the refractive index of the overall alumina particles (d) can be expressed as a weighted average refractive index, and it is desired that the average refractive index is from 1.60 to 1.70, and preferably from 1.60 to 1.65. In the present specification, the refractive index of the alumina particles is measured in accordance with the method described in Examples set forth below.

In general, transparency of the composite resin also depends on the particle size of a filler, besides the difference between the refractive indices of the filler such as alumina particles and the polymerizable monomer composition. In addition, the more the wavelength of light and the particle size of the particles constituting the matrix of the composition of dental use approximates, the larger the light scattering, so that transparency is likely to be lowered. In view of the above, when particles having particles sizes that are greatly different from the visible range of 0.4 to 0.7 μm are used, the extent of light scattering can be reduced and the transparency can be maintained; however, when a proportion of particles having particle sizes approximating the visible light range of greater than 0.1 μm is large, there is a tendency that it is difficult to obtain a desired transparency especially in the alumina particles. On the other hand, when a proportion of particles having particle sizes smaller than 0.005 μm is larger, the viscosity of the matrix increases, so that handling property may be impaired in some cases. Therefore, the alumina particles (d) used in the present invention have a proportion of particles having particle sizes of from 0.005 to 0.1 μm of preferably 95% by number or more, and more preferably 99% by number or more. Here, in the present specification, the proportion of the number of the particles of the alumina particles is measured in accordance with the method described in Examples set forth below.

The alumina particles (d) are obtained by a vapor phase combustion method of aluminum chloride, a method comprising combusting at a temperature of from 400° to 1000° C. an alumina hydrated gel obtained by hydrolysis of an organic aluminum salt, or obtained by spark discharge of aluminum in water.

The alumina particles (d) may be blended with other constituents after subjecting the particles to a surface treatment. As the surface treatment agent, a silane coupling agent, an organic titanate-based coupling agent, an organic aluminum-based coupling agent, or the like is used. Among them, a coupling agent having a functional group capable of copolymerizing with the polymerizable monomers is preferred. For example, vinyl trichlorosilane, vinyl triethoxysilane, γ-methacryloxypropyl trimethoxysilane, γ-mercaptopropyl trimethoxysilane, isopropyl isostearoyldiacryl titanate, tetra(2,2-diallyloxymethyl-1-butyl) bis(di-tridecyl) phosphite titanate, or the like is preferred. It is preferable that these coupling agents are added in an amount of preferably from 5 to 100 parts by weight, based on 100 parts by weight of the alumina particles.

The alumina particles (d) are contained in an amount of preferably from 7.5 to 50% by weight, and more preferably from 7.5 to 20% by weight, of the composition for dental use.

When the ratio of the weight of all the polymerizable monomers to the weight of the alumina particles, i.e. all the polymerizable monomers/alumina particles, is less than 1.5, a change in transparency before and after the polymerization becomes large, and when the ratio exceeds 2.5, kneading becomes difficult, thereby making it likely to lower the handling property of the composition. In view of the above, the ratio of WM, a total weight of the polymerizable monomers (a), (b) and (c) and WA, a weight of the alumina particles (d), i.e. WA/WM, is preferably from 1.5 to 2.5, and more preferably from 1.5 to 2.0.

Further, it is preferable that the composition for dental use of the present invention contains specified inorganic particles (e) other than the alumina particles (d), from the viewpoint of further improving mechanical strength and wear resistance.

In the case where the inorganic particles (e) other than the alumina particles (d) in the present invention are used, it is desirable to select inorganic particles satisfying the three requirements:

(iii) a refractive index ($n_F$) is from 1.50 to 1.65,
(iv) a proportion of particles having particle sizes of from 0.01 to 100 µm is 95% by volume or more, and
(v) a volume-median particle size is from 0.1 to 20 µm.

Since it is preferable that the polymerizable monomers have a refractive index after the polymerization of from 1.5 to 1.7, and that the alumina particles (d) have a refractive index of from 1.60 to 1.70, it is preferable that the inorganic particles (e) having a refractive index approximating the above range is selected, from the viewpoint of transparency. In other words, it is desired that the inorganic particles (e) have a refractive index of preferably from 1.50 to 1.65, and more preferably from 1.53 to 1.60. The refractive index of the inorganic particles (e) as used herein is measured in accordance with the method described in Examples set forth below.

The inorganic particles (e) having the above refractive index include glass materials, such as strontium borosilicate glass ($n_F$=1.50, Ray-Sorb (registered trademark) T-4000, manufactured by Kimble), barium borosilicate glass ($n_F$=1.553, Ray-Sorb (registered trademark) E-3000, manufactured by Specialty Glass), barium silicate glass ($n_F$=1.58, Ray-Sorb (registered trademark) E-2000, manufactured by Specialty Glass), and lanthanum glass ceramics ($n_F$=1.579, GM31684, manufactured by Shott); inorganic salts insoluble in water, such as hydroxyapatite ($n_F$=1.61 to 1.63) and calcium phosphate ($n_F$=1.60); and the like.

Further, it is preferable that the material for the inorganic particles (e) used in the present invention has radiopacity. Radiopacity that is significant in dental diagnosis is defined as "radiopacity of the same level as or higher than an aluminum plate having the same thickness as a test material," and the inorganic particles giving the radiopacity as described above generally contain an element heavier than potassium. The inorganic particles giving the radiopacity include, for example, inorganic particles of calcium, titanium, iron, zinc, strontium, zirconium, tin, barium, lanthanum, cerium, ytterbium, hafnium, tungsten, and the like.

In addition, from the viewpoint of operability of shaping the form of the teeth and shape reproducibility (or restorability), it is preferable that the inorganic particles (e) have a proportion of particles having particle sizes of from 0.01 to 100 µm of 95% by volume or more, and preferably 99% by volume or more, and that the inorganic particles have a particle size distribution that a volume-median particle size is from 0.1 to 20 µm, and preferably from 0.5 to 10 µm. Specifically, the inorganic particles (e) having a desired particle size distribution as mentioned above can be obtained by classifying the inorganic particles, and reducing the content of fine powder and coarse particles, thereby adjusting to give a sharp particle size distribution. In general, when a proportion of particles having particle sizes smaller than 0.01 µm is large, mechanical strength is weakened, and when a proportion of particles having particle sizes greater than 100 µm is large, a composition past for dental use has a rough texture, thereby impairing the handling property. Here, the volume-median particle size and the proportion of the number of the particles of the inorganic particles (e) as used herein are measured in accordance with the methods described in Examples set forth below.

The inorganic particles (e) having the above particle size distribution can be easily produced by subjecting the inorganic particles having the above refractive index to a known grinding or milling procedure, or to a precipitate-formation method by a solution reaction, and the shape thereof may be any of disintegrated form, spherical form, scaly form, but not particularly limited thereto.

The inorganic particles (e) may be blended with other constituents after subjecting the particles to a surface treatment. The surface treatment agent includes the same ones as the coupling agents mentioned above, and the surface treatment agent is added in an amount of from 0.1 to 10 parts by weight, based on 100 parts by weight of the inorganic particles.

The inorganic particles (e) are contained in an amount of preferably from 30.0 to 87.5% by weight, and more preferably from 65.0 to 87.5% by weight, of the composition for dental use.

In addition, from the viewpoint of mechanical strength, WM, a total weight of the polymerizable monomers (a), (b) and (c), WA, a weight of the alumina particles (d), and WF, a weight of the inorganic particles (e) preferably satisfy the following formula:

$$[(WF+WA)/(WM+WA+WF)] \times 100 \geq 80,$$

and more preferably satisfy the following formula:

$$[(WF+WA)/(WM+WA+WF)] \times 100 \geq 85.$$

When the total weight of the alumina particles (d) and the inorganic particles (e) is 80% by weight or more of the total weight of the polymerizable monomers (a), (b) and (c), the alumina particles (d), and the inorganic particles (e), the composition for dental use of the present invention has excellent mechanical strength and is preferred.

In the present invention, besides the polymerizable monomers (a), (b) and (c), the alumina particles (d), and the inorganic particles (e) other than the alumina particles (d), an additive such as an organic-inorganic composite filler, a pigment, an ultraviolet absorbent, a fluorescent agent, or a polymerization inhibitor may be blended as raw materials.

The ultraviolet absorbent includes, for example, 2-hydroxy-4-t-butoxybenzophenone and 2-(3-t-butyl-5-methyl-2-hydroxyphenyl)-5-chlorobenzotriazole. The polymerization inhibitor includes, for example, 2,6-di-butylhydroxytoluene, hydroquinone, dibutylhydroquinone, dibutylhydroquinone monomethyl ether, and 2,6-t-butylphenol.

The composition of the present invention is not particularly limited so long as the composition contains the polymerizable monomers (a), (b) and (c) in given amounts, and the composition can be easily produced by a method known to one of ordinary skill in the art.

EXAMPLES

[Refractive Index]

The refractive index is measured by a liquid immersion method using Abbe's refractometer with sodium D rays as a light source, using diiodomethane, bromonaphthalene, methyl salicylate, dimethyl formamide, or the like, each in which sulfur is dissolved, as a solvent. Here, a refractive index after the polymerization of the polymerizable monomer is measured by using a product obtained by defoaming a polymerizable monomer dissolved in camphorquinone, subjecting a defoamed polymerizable monomer to photopolymerization to cure, and molding a cured product into a rectangular parallelepiped having a size of 5 mm×10 mm×20 mm as a test piece.

[Proportion of Number of Particles of Alumina Particles]

To a polymerizable monomer prepared by dissolving 1 part by weight of 2,4,6-trimethylbenzoyl diphenyl phosphine oxide in 100 parts by weight of triethylene glycol dimethacrylate are mixed with 10 parts by weight of fine alumina powder, to prepare a paste. The paste is subjected to polymerization by photoirradiation to cure, and a cured product is sliced with an ultramicrotome to prepare sample sliced pieces, and the sample sliced pieces are subjected to TEM observation (magnification: 200,000 folds) and photographed with a transmission electron microscope (Model: H-800NA, manufactured by HITACHI, LTD.). Two-hundred particles that are captured in the photograph are randomly chosen, and the sizes of the particles are measured to obtain a particle size distribution. From the particle size distribution obtained, the proportion of the number of the particles having particle sizes of from 0.005 to 0.1 µm is obtained. Here, the particle size of the fine alumina powder as used herein is an arithmetic means of the longest length and the shortest length of the particles.

[Volume-Median Particle Size and Proportion of Number of Particles of Inorganic Particles Other than Alumina Particles]

The volume-median particle size means a particle size of which cumulative volume frequency calculated in volume percentage is 50% calculated from a smaller particle size side.
Measurement Apparatus Particle Size Distribution Analyzer SALD-2100 (manufactured by Shimadzu Corporation)
Analyzing Software: WingSALD
Dispersion: 0.2% sodium hexamethaphosphate
Dispersion Conditions: A 15 mg sample is added to 20 mL of the above dispersion, and the mixture is dispersed with an ultrasonic disperser for 20 minutes to prepare a sample-containing dispersion.
Measurement Conditions The above sample-containing dispersion is measured to obtain a volume-median particle size and a proportion of the number of the particles having particle sizes of from 0.01 to 100 µm.

Production Example 1 of Alumina Particles

Twenty parts by weight of γ-methacryloxypropyl trimethoxysilane were added to 100 parts by weight of ultrafine alumina particles "Aluminum Oxide C" (manufactured by Nihon Aerosil Co., Ltd.) having an average particle size of 0.02 µm, a proportion of the number of the particles having particle sizes of from 0.005 to 0.1 µm of 99% by number, and a refractive index of 1.65, while mixing, to give surface-treated alumina particles A-1. Here, the alumina particles A-1 had a refractive index of 1.65.

Production Example 1 of Inorganic Particles Other than Alumina Particles

Lanthanum glass ceramics "GM31684" (manufactured by Shott) were ground or milled with a vibration ball-mill, to obtain a fine inorganic particles powder having a volume-median particle size of 1.2 µm and a proportion of the number of the particles having particle sizes of from 0.01 to 100 µm of 99% by volume.

Two parts by weight of γ-mercaptopropyl trimethoxysilane were added to 100 parts by weight of the fine inorganic particles powder obtained while mixing, to give surface-treated inorganic particles F-1. Here, the inorganic particles F-1 had a refractive index of 1.58.

Production Example 2 of Inorganic Particles Other than Alumina Particles

Fluoroaluminosilicate "GM35429" (manufactured by Shott) was ground or milled with a vibration ball-mill, to obtain a fine inorganic particles powder having a volume-median particle size of 1.8 µm and a proportion of the number of the particles having particle sizes of from 0.01 to 100 µm of 99% by volume.

Two parts by weight of γ-mercaptopropyl trimethoxysilane were added to 100 parts by weight of the fine inorganic particles powder obtained while mixing, to give surface-treated inorganic particles F-2. Here, the inorganic particles F-2 had a refractive index of 1.47.

Examples 1 to 12 and Comparative Examples 1 to 11

To 100 parts by weight of a mixture of the polymerizable monomers (a), (b) and (c) shown in Table 1 or 2 were added 0.5 parts by weight of a photopolymerization initiator dl-camphorquinone, and 1.0 part by weight of ethyl 4-dimethylaminobenzoate to dissolve, to prepare a photopolymerizable composition.

A mixture prepared by mixing the alumina particles shown in Table 1 or 2, and inorganic particles with 100 parts by weight of the photopolymerizable composition obtained and kneading the mixture to a homogeneous mixture was subjected to vacuum defoaming, to give each of compositions for dental use of Examples 1 to 12 and Comparative Examples 1 to 11.

Here, the abbreviations shown in Tables 1 and 2 mean the following.
Bis-GMA: 2,2-Bis[4-[3-(meth)acryloyloxy-2-hydroxypropoxy]phenyl]propane
Bis 3: 2-[4-[3-(meth)acryloyloxy-2-hydroxypropoxy]phenyl]-2-[4-[2,3-di(meth)acryloyloxypropoxy]phenyl]propane
D2.6E: 2,2-Bis[4-(meth)acryloyloxypolyethoxyphenyl]propane (average number of moles of ethoxy groups added: 2.6)
D6E: 4-(Meth)acryloyloxypolyethoxyphenyl]propane (average number of moles of ethoxy groups added: 6)
3G: Triethylene glycol di(meth)acrylate
DD: 1,10-Decanediol di(meth)acrylate
UDMA: N,N'-(2,2,4-Trimethylhexamethylene)bis[2-(aminocarboxy)ethan-1-ol]di(meth)acrylate Next, the physical properties of the compositions for dental use obtained were examined in accordance with the methods of Test Examples 1 to 6 set forth below. The results are shown in Tables 1 and 2.

Test Example 1

Compressive Strength

Test pieces (4 mmφ×4 mm) of the compositions of dental use were prepared. Each of the test pieces was immersed in water at 37° C. for 24 hours, and compressive strength was measured using a tensile tester (manufactured by Instron) by setting a crosshead speed at 2 mm/min. Here, those having a compressive strength of 350 MPa or more were judged to be excellent.

Test Example 2

Flexural Strength

Test pieces (2 mm×2 mm×30 mm) of the compositions of dental use were prepared. Each of the test pieces was immersed in water at 37° C. for 24 hours, and flexural strength was measured using a tensile tester (manufactured by Instron) by setting a crosshead speed at 1 mm/min in accordance with a three-point flexural test method at a span of 2.5 mm. Here, those having a flexural strength of 120 MPa or more were judged to be excellent.

Test Example 3

Operability

A composition for dental use was filled in a hole of 4 mmφ×4 mm, and the operability was evaluated from the viewpoint of ease in filling operation of the paste property in accordance with the following evaluation criteria.

<Evaluation Criteria of Operability>

A: The paste is not tacky or dry, being excellent in filling operation.
B: Although the paste is slightly tacky or dry, the filling operation is facilitated.
C: The paste is strongly tacky or dry, thereby making the filling operation difficult.

Here, those with ranks A and B are practically utilizable levels.

Test Example 4

Transparency

Test pieces (20 mmφ×1.0 mm) of the compositions of dental use were prepared. The brightness (L1) of a case where the chromaticity was measured by placing a standard whiteboard in the background of a test piece, and the brightness (L2) of a case where the chromaticity was measured by placing a standard blackboard in the background of the same test piece were measured, and a difference therebetween (ΔL=L1−L2) was calculated and used as an index for transparency. The larger the value of ΔL, the higher the transparency, and those having ΔL of 15 or more were judged to be excellent.

Test Example 5

Change in Transparency Before and After Polymerization

A composition paste for dental use was placed on a cover glass, and a ring-shaped die having a diameter of 20 mm and a thickness of 1 mm was placed thereon, and a different cover glass was placed thereover, and pressed, and transparency (ΔL1) was measured in the same manner as in Test Example 4 using a spectrophotometer (CM-3610d, manufactured by Minolta). Next, the composition paste held between cover glass was subjected to photoirradiation for 20 seconds using a photoirradiation device for dental use ("JETLITE 3000" manufactured by MORITA) to polymerize, and transparency (ΔL2) was measured for colorimetry in the same manner. The change in transparency before and after the irradiation was expressed by Δ(ΔL)=(ΔL2−ΔL1), and used as an index for a change in transparency before and after the polymerization. In this evaluation method, the smaller the Δ(ΔL), the smaller the change in transparency before and after the polymerization.

Test Example 6

Adhesive Properties

Bovine front teeth were smoothly subjected to wet grinding with #1000 Silicon Carbide Paper (manufactured by Nihon Kenshi Co., Ltd.) to expose an enamel surface or a dentine surface, and water on the surface was then blown away with an air syringe for dental use. To the exposed enamel surface or the dentine surface was adhered an adhesive tape having a circular hole having a diameter of 3 mm, the adhesive tape having a thickness of about 150 μm, and an adhesive composition for dental use (trade name "CLEARFIL S³BOND," manufactured by Kuraray Medical Inc.) was applied to the circular hole with a brush, and the coating was allowed to stand for 20 seconds, and then dried with an air syringe for dental use until there was no fluidity of the adhesive composition for dental use. Next, the dried coating was photoirradiated with a photoirradiation device for dental use (trade name "JETLITE 3000," manufactured by MORITA) for 10 seconds. Thereafter, the composition for dental use prepared above was placed on the dried adhesive composition for dental use, and covered with a releasing film (trade name "EVAL," manufactured by Kuraray Co., Ltd.), and a slide glass was placed on the releasing film and pressed. The composition was subjected to photoirradiation with the above photoirradiation device for dental use for 20 seconds, to cure a composition for dental use. Thereafter, one end side (circular cross section) of a stainless steel cylindrical rod having a diameter of 5 mm and a length of 1.5 cm was adhered to a cured surface using a resin cement for dental use (trade name "PANAVIA 21," manufactured by Kuraray Medical Inc.), and allowed to stand for 30 minutes, to provide a test piece. The test piece was allowed to stand for 24 hours in a thermostat at 37° C. in a state that the test piece was immersed in distilled water in the sample vessel, and thereafter subjected to a measurement of bond strength. Here, in the measurement of bond strength (tensile bond strength), a tensile tester (manufactured by Intron) was used, and the measurement was taken by setting a crosshead speed to 2 mm/min. Here, those having bond strength of 15 MPa or more were judged to be excellent.

TABLE 1

| Components of Compositions for Dental Use | Examples | | | | | | |
|---|---|---|---|---|---|---|---|
| | 1 | 2 | 3 | 4 | 5 | 6 | 7 |
| Polymerizable Monomer (a) | Bis-GMA | Bis-GMA | Bis-GMA | Bis-GMA | Bis-GMA | Bis-GMA | Bis-GMA |
| Polymerizable Monomer (b) | D2.6E | D2.6E | D2.6E | D2.6E | D2.6E | D2.6E | D2.6E |
| Polymerizable Monomer (c) | 3G | 3G | 3G | 3G | 3G | 3G | 3G |
| Weight Ratio of Monomers (a/b) | 0.33 | 0.33 | 0.33 | 0.33 | 0.33 | 0.19 | 0.51 |
| Weight Ratio of Monomers (a/c) | 1.00 | 1.00 | 1.00 | 1.00 | 1.00 | 0.65 | 1.35 |
| Weight Ratio of Monomers (a/b/c) | 20/60/20 | 20/60/20 | 20/60/20 | 20/60/20 | 20/60/20 | 13/67/20 | 27/53/20 |
| Refractive Index After Curing | 1.56 | 1.56 | 1.56 | 1.56 | 1.56 | 1.56 | 1.56 |
| Amount Formulated (Parts by Weight) (WM) | 100 | 100 | 100 | 100 | 100 | 100 | 100 |
| Alumina Particles | A-1 | A-1 | A-1 | A-1 | A-1 | A-1 | A-1 |

TABLE 1-continued

| | | | | | | | |
|---|---|---|---|---|---|---|---|
| Amount Formulated (Parts by Weight) (WA) | 200 | 130 | 270 | 200 | 200 | 200 | 200 |
| Inorganic Particles | F-1 | F-1 | F-1 | F-1 | F-2 | F-1 | F-1 |
| Amount Formulated (Parts by Weight) (WF) | 800 | 800 | 800 | 190 | 800 | 800 | 800 |
| Relational Formula | | | | | | | |
| WA/WM | 2 | 1.3 | 2.7 | 2 | 2 | 2 | 2 |
| [(WA + WF)/(WA + WM + WF)] × 100 | 90.9 | 90.3 | 91.5 | 79.6 | 90.9 | 90.9 | 90.9 |
| Physical Properties | | | | | | | |
| Compressive Strength (MPa) | 510 | 480 | 502 | 356 | 490 | 481 | 457 |
| Flexural Strength (MPa) | 178 | 156 | 183 | 143 | 188 | 170 | 165 |
| Operability | A | A | B | A | A | A | B |
| Transparency (ΔL) | 24 | 26 | 18 | 23 | 16 | 22 | 21 |
| Change in Transparency (ΔL) Before and After Polymerization | 0.6 | 2.0 | 0.3 | 0.9 | 1.2 | 1.0 | 0.8 |
| Bond Strength (MPa) | 19 | 17 | 18 | 18 | 17 | 15 | 20 |

| Components of Compositions for Dental Use | Examples | | | | |
|---|---|---|---|---|---|
| | 8 | 9 | 10 | 11 | 12 |
| Polymerizable Monomer (a) | Bis-GMA | Bis-GMA | Bis3 | Bis-GMA | Bis-GMA |
| Polymerizable Monomer (b) | D2.6E | D2.6E | D2.6E | D6E | D2.6E |
| Polymerizable Monomer (c) | 3G | 3G | 3G | 3G | DD |
| Weight Ratio of Monomers (a/b) | 0.45 | 0.22 | 0.33 | 0.33 | 0.33 |
| Weight Ratio of Monomers (a/c) | 2.08 | 0.48 | 1.00 | 1.00 | 1.00 |
| Weight Ratio of Monomers (a/b/c) | 27/60/13 | 13/60/27 | 20/60/20 | 20/60/20 | 20/60/20 |
| Refractive Index After Curing | 1.56 | 1.55 | 1.56 | 1.56 | 1.56 |
| Amount Formulated (Parts by Weight) (WM) | 100 | 100 | 100 | 100 | 100 |
| Alumina Particles | A-1 | A-1 | A-1 | A-1 | A-1 |
| Amount Formulated (Parts by Weight) (WA) | 200 | 200 | 200 | 200 | 200 |
| Inorganic Particles | F-1 | F-1 | F-1 | F-1 | F-1 |
| Amount Formulated (Parts by Weight) (WF) | 800 | 800 | 800 | 800 | 800 |
| Relational Formula | | | | | |
| WA/WM | 2 | 2 | 2 | 2 | 2 |
| [(WA + WF)/(WA + WM + WF)] × 100 | 90.9 | 90.9 | 90.9 | 90.9 | 90.9 |
| Physical Properties | | | | | |
| Compressive Strength (MPa) | 445 | 437 | 499 | 437 | 410 |
| Flexural Strength (MPa) | 163 | 175 | 180 | 161 | 169 |
| Operability | B | A | A | A | A |
| Transparency (ΔL) | 22 | 22 | 22 | 20 | 21 |
| Change in Transparency (ΔL) Before and After Polymerization | 0.9 | 1.5 | 0.9 | 0.8 | 0.5 |
| Bond Strength (MPa) | 17 | 16 | 18 | 17 | 15 |

TABLE 2

| Components of Compositions for Dental Use | Comparative Examples | | | | | |
|---|---|---|---|---|---|---|
| | 1 | 2 | 3 | 4 | 5 | 6 |
| Polymerizable Monomer (a) | — | Bis-GMA | — | Bis-GMA | Bis-GMA | Bis-GMA |
| Polymerizable Monomer (b) | D2.6E | — | D2.6E | D2.6E | D2.6E | — |
| Polymerizable Monomer (c) | 3G, UDMA | 3G, UDMA | 3G | 3G | 3G | 3G |
| Weight Ratio of Monomers (a/b) | 0.00 | — | 0.00 | 0.80 | 0.08 | — |
| Weight Ratio of Monomers (a/c) | 0.00 | 0.25 | 0.00 | 4.00 | 0.17 | 233 |
| Weight Ratio of Monomers (a/b/c) | 0/60/40[*1] | 20/0/80[*2] | 0/70/30 | 40/50/10 | 5/65/30 | 70/0/30 |
| Refractive Index After Curing | 1.52 | 1.53 | 1.55 | 1.56 | 1.55 | 1.56 |
| Amount Formulated (Parts by Weight) (WM) | 100 | 100 | 100 | 100 | 100 | 100 |
| Alumina Particles | A-1 | A-1 | A-1 | A-1 | A-1 | A-1 |
| Amount Formulated (Parts by Weight) (WA) | 200 | 200 | 200 | 200 | 200 | 200 |
| Inorganic Particles | F-1 | F-1 | F-1 | F-2 | F-1 | F-1 |
| Amount Formulated (Parts by Weight) (WF) | 800 | 800 | 380 | 800 | 800 | 800 |
| Relational Formula | | | | | | |
| WA/WM | 2 | 2 | 2 | 2 | 2 | 2 |
| [(WA + WF)/(WA + WM + WF)] × 100 | 90.9 | 90.9 | 85.3 | 90.9 | 90.9 | 90.9 |
| Physical Properties | | | | | | |
| Compressive Strength (MPa) | 486 | 425 | 203 | 425 | 300 | 473 |
| Flexural Strength (MPa) | 180 | 165 | 80 | 163 | 155 | 169 |
| Operability | A | C | B | B | A | C |
| Transparency (ΔL) | 22 | 25 | 21 | 10 | 21 | 20 |
| Change in Transparency (ΔL) Before and After Polymerization | 0.3 | 0.8 | 3 | 0.5 | 3.2 | 1.3 |
| Bond Strength (MPa) | 8 | 11 | 4 | 17 | 7 | 16 |

| Components of Compositions for Dental Use | Comparative Examples | | | | |
|---|---|---|---|---|---|
| | 7 | 8 | 9 | 10 | 11 |
| Polymerizable Monomer (a) | Bis-GMA | Bis-GMA | Bis-GMA | Bis-GMA | Bis-GMA |
| Polymerizable Monomer (b) | D2.6E | D2.6E | D2.6E | D2.6E | D2.6E |
| Polymerizable Monomer (c) | 3G | 3G | — | 3G | 3G |
| Weight Ratio of Monomers (a/b) | 0.13 | 0.75 | 0.43 | 0.2 | 0.46 |
| Weight Ratio of Monomers (a/c) | 1.00 | 1.00 | — | 0.25 | 6.00 |
| Weight Ratio of Monomers (a/b/c) | 10/80/10 | 30/40/30 | 30/70/0 | 10/50/40 | 30/65/5 |
| Refractive Index After Curing | 1.56 | 1.55 | 1.57 | 1.55 | 1.57 |
| Amount Formulated (Parts by Weight) (WM) | 100 | 100 | 100 | 100 | 100 |
| Alumina Particles | A-1 | A-1 | A-1 | A-1 | A-1 |
| Amount Formulated (Parts by Weight) (WA) | 200 | 200 | 200 | 200 | 200 |
| Inorganic Particles | F-1 | F-1 | F-1 | F-1 | F-1 |
| Amount Formulated (Parts by Weight) (WF) | 800 | 800 | 800 | 800 | 800 |
| Relational Formula | | | | | |
| WA/WM | 2 | 2 | 2 | 2 | 2 |
| [(WA + WF)/(WA + WM + WF)] × 100 | 90.9 | 90.9 | 90.9 | 90.9 | 90.9 |

TABLE 2-continued

| Physical Properties | | | | | |
|---|---|---|---|---|---|
| Compressive Strength (MPa) | 404 | 228 | 255 | 242 | 311 |
| Flexural Strength (MPa) | 148 | 125 | 131 | 120 | 152 |
| Operability | B | A | C | A | B |
| Transparency (ΔL) | 10 | 19 | 5 | 23 | 8 |
| Change in Transparency (ΔL) Before and After Polymerization | 1 | 4.5 | 0.4 | 8 | 0.6 |
| Bond Strength (MPa) | 9 | 16 | 12 | 10 | 14 |

*1 The ratio of the weight of 3G to the weight of UDMA, i.e. 3G/UDMA, is 20/20.
*2 The ratio of the weight of 3G to the weight of UDMA, i.e. 3G/UDMA, is 20/60.

It can be seen from the above results that the compositions for dental use of Examples have smaller changes in transparency before and after the polymerization and excellent mechanical strength, adhesive properties and operability, as compared to the compositions for dental use of Comparative Examples, by specifying the kinds and the compositional ratios of the polymerizable monomers. In particular, it can be seen from the comparison of Examples 1 to 4 that even with the same components of the polymerizable monomers, those having larger contents of the alumina particles and the inorganic particles have stronger mechanical strength, and those having smaller content of the alumina particles have excellent operability. Also, it can be seen from the comparison of Examples 1 to 3 that those having larger contents of the alumina particles have smaller changes in transparency before and after the polymerization. On the other hand, it can be seen that in Comparative Example 1 where UDMA that does not have an aromatic ring or a hydroxyl group is used in place of the polymerizable monomer (a), bond strength is weakened, that in Comparative Example 9 where only the polymerizable monomers (a) and (b) are used, transparency of the compositions is lowered, and that in Comparative Examples 4, 5, 7, 8, 10 and 11 where the polymerizable monomers (a), (b) and (c) are used but each content is outside the defined range, various physical properties are deteriorated, such as transparency of the compositions is lower, and changes in transparency before and after the polymerization are larger. It is suggested from the above results that since the composition contains the polymerizable monomers (a), (b) and (c) in a well-balanced specified ratio in which the monomer (b) is contained in a larger amount, the composition has excellent mechanical strength, adhesive properties and operability, and further allows the composition to have a high transparency and a small change in transparency before and after the polymerization. In particular, as is clear from the comparison of Examples 1, 8, and 9, in a case where a/c is 1, even with the same components used, it can be seen that the composition shows the most excellent physical properties.

INDUSTRIAL APPLICABILITY

The composition for dental use of the present invention can be suitably used as a product capable of substituting a part or all of a natural tooth in the field of dental therapy.

The invention claimed is:

1. A composition, comprising:
   a polymerizable monomer (a) comprising an aromatic ring and a hydroxyl group;
   a polymerizable monomer (b) comprising an aromatic ring and no hydroxyl groups;
   a polymerizable monomer (c) other than the polymerizable monomers (a) and (b); and
   alumina particles (d),
   wherein the composition comprises the polymerizable monomers (a), (b), and (c) in an amount of from 10 to 30% by weight, from 50 to 70% by weight, and from 10 to 30% by weight, respectively, of all the polymerizable monomers,
   wherein the alumina particles (d) satisfy requirements (i) and (ii):
   (i) a refractive index ($n_A$) is from 1.60 to 1.70; and
   (ii) a proportion of particles having particle sizes of from 0.005 to 0.1 μm is 95% by number or more, and
   wherein a ratio of WA, a weight of the alumina particles (d), and WM, a total weight of the polymerizable monomers (a), (b), and (c), WA/WM, is from 1.5 to 2.5.

2. The composition of claim 1, wherein the polymerizable monomer (a) is a compound comprising a bisphenol A backbone and a hydroxyl group, and wherein the polymerizable monomer (b) is a compound comprising a bisphenol A backbone and no hydroxyl groups.

3. The composition of claim 1, further comprising inorganic particles (e) other than the alumina particles (d), wherein the inorganic particles (e) satisfy requirements (iii), (iv), and (v):
   (iii) a refractive index ($n_F$) is from 1.50 to 1.65;
   (iv) a proportion of particles having particle sizes of from 0.01 to 100 μm is 95% by volume or more; and
   (v) a volume-median particle size is from 0.1 to 20 μm.

4. The composition of claim 3, wherein WM, a total weight of the polymerizable monomers (a), (b), and (c), WA, a weight of the alumina particles (d), and WF, a weight of the inorganic particles (e) satisfy:

$$[(WF+WA)/(WM+WA+WF)] \times 100 \geq 80.$$

5. The composition of claim 2, further comprising inorganic particles (e) other than the alumina particles (d), wherein the inorganic particles (e) satisfy requirements (iii), (iv), and (v):
   (iii) a refractive index ($n_F$) is from 1.50 to 1.65;
   (iv) a proportion of particles having particle sizes of from 0.01 to 100 μm is 95% by volume or more; and
   (v) a volume-median particle size is from 0.1 to 20 μm.

6. The composition of claim 5, wherein WM, a total weight of the polymerizable monomers (a), (b), and (c), WA, a weight of the alumina particles (d), and WF, a weight of the inorganic particles (e) satisfy:

$$[(WF+WA)/(WM+WA+WF)] \times 100 \geq 80.$$

7. A method of substituting a part or all of a natural tooth, the method comprising:
(A) filling a cavity of a natural tooth with a composition comprising
at least one polymerizable monomer (a) comprising an aromatic ring and a hydroxyl group,
at least one polymerizable monomer (b) comprising an aromatic ring and no hydroxyl groups,
at least one polymerizable monomer (c) other than the polymerizable monomers (a) and (b), and
alumina particles (d),
wherein the composition comprises the polymerizable monomers (a), (b), and (c) in an amount of from 10 to 30% by weight, from 50 to 70% by weight, and from 10 to 30% by weight, respectively, of all the polymerizable monomers
wherein the alumina particles (d) satisfy requirements (i) and (ii):
(i) a refractive index ($n_A$) is from 1.60 to 1.70; and
(ii) a proportion of particles having particle sizes of from 0.005 to 0.1 μm is 95% by number or more, and
wherein a ratio of WA, a weight of the alumina particles (d), and WM, a total weight of the polymerizable monomers (a), (b), and (c), WA/WM, is from 1.5 to 2.5; and
(B) curing the composition.

8. A method of preparing a composition operable for substituting a part or all of a natural tooth, the method comprising:
(A) mixing components comprising
at least one polymerizable monomer (a) comprising an aromatic ring and a hydroxyl group,
at least one polymerizable monomer (b) comprising an aromatic ring and no hydroxyl groups,
at least one polymerizable monomer (c) other than the polymerizable monomers (a) and (b), and
alumina particles (d), to obtain the composition,
wherein the composition comprises the polymerizable monomers (a), (b), and (c) in an amount of from 10 to 30% by weight, from 50 to 70% by weight, and from 10 to 30% by weight, respectively, of all the polymerizable monomers,
wherein the alumina particles (d) satisfy requirements (i) and (ii):
(i) a refractive index ($n_A$) is from 1.60 to 1.70; and
(ii) a proportion of particles having particle sizes of from 0.005 to 0.1 μm is 95% by number or more, and
wherein a ratio of WA, a weight of the alumina particles (d), and WM, a total weight of the polymerizable monomers (a), (b), and (c), WA/WM, is from 1.5 to 2.5.

9. The composition of claim 1, wherein the composition is suitable for substituting a part or all of a natural tooth.

\* \* \* \* \*